United States Patent [19]
Yamashita et al.

[11] Patent Number: 5,096,173
[45] Date of Patent: Mar. 17, 1992

[54] MEDICAL TREATMENT TABLE WITH PASSIVE RESTRAINTS

[76] Inventors: Kunio Yamashita, 212 S. 7th St., Central Point, Oreg. 97502; Valerie S. Lathrop, 135 Fern Valley Rd. #60, Medford, Oreg. 97501

[21] Appl. No.: 548,754

[22] Filed: Jul. 5, 1990

[51] Int. Cl.$^5$ .............................. A61G 13/00
[52] U.S. Cl. .............................. 269/328
[58] Field of Search ............ 5/431, 434, 437; 128/869, 870, 70, 71, 75; 269/328, 900, 305

[56] References Cited

U.S. PATENT DOCUMENTS

| | | | |
|---|---|---|---|
| 2,678,857 | 5/1954 | Hans | 269/328 |
| 3,286,693 | 11/1966 | Clarke et al. | 128/870 |
| 3,829,079 | 8/1974 | Fox | 269/328 |
| 3,892,399 | 7/1975 | Cabansag | 128/870 |
| 4,616,814 | 10/1986 | Harwood-Nash | 269/328 |
| 4,672,952 | 6/1987 | Vrzalik | 128/870 |
| 4,771,493 | 9/1988 | Park | 269/328 |

Primary Examiner—Robert C. Watson
Attorney, Agent, or Firm—James D. Givnan, Jr.

[57] ABSTRACT

A medical table having a multitude of restraint assemblies adjustably mounted thereon against which the torso and legs of a patient may be placed to prevent undesired movement during treatment. Each restraint assembly includes a control knob which positions a foot member into and out of engagement with a pair of retainers on the underside of the table top member. Openings in the table top member permit horizontal positioning of the restraint assemblies to accommodate children and adult patients and the positioning required for the medical procedure to be accomplished. A secondary restraint carried by certain of the restraint assemblies includes arms which prohibit vertical movement of the patient. The retainers are arranged in pairs on the underside of the table top member and include teeth for locking engagement with the foot member of each restraint assembly.

9 Claims, 1 Drawing Sheet

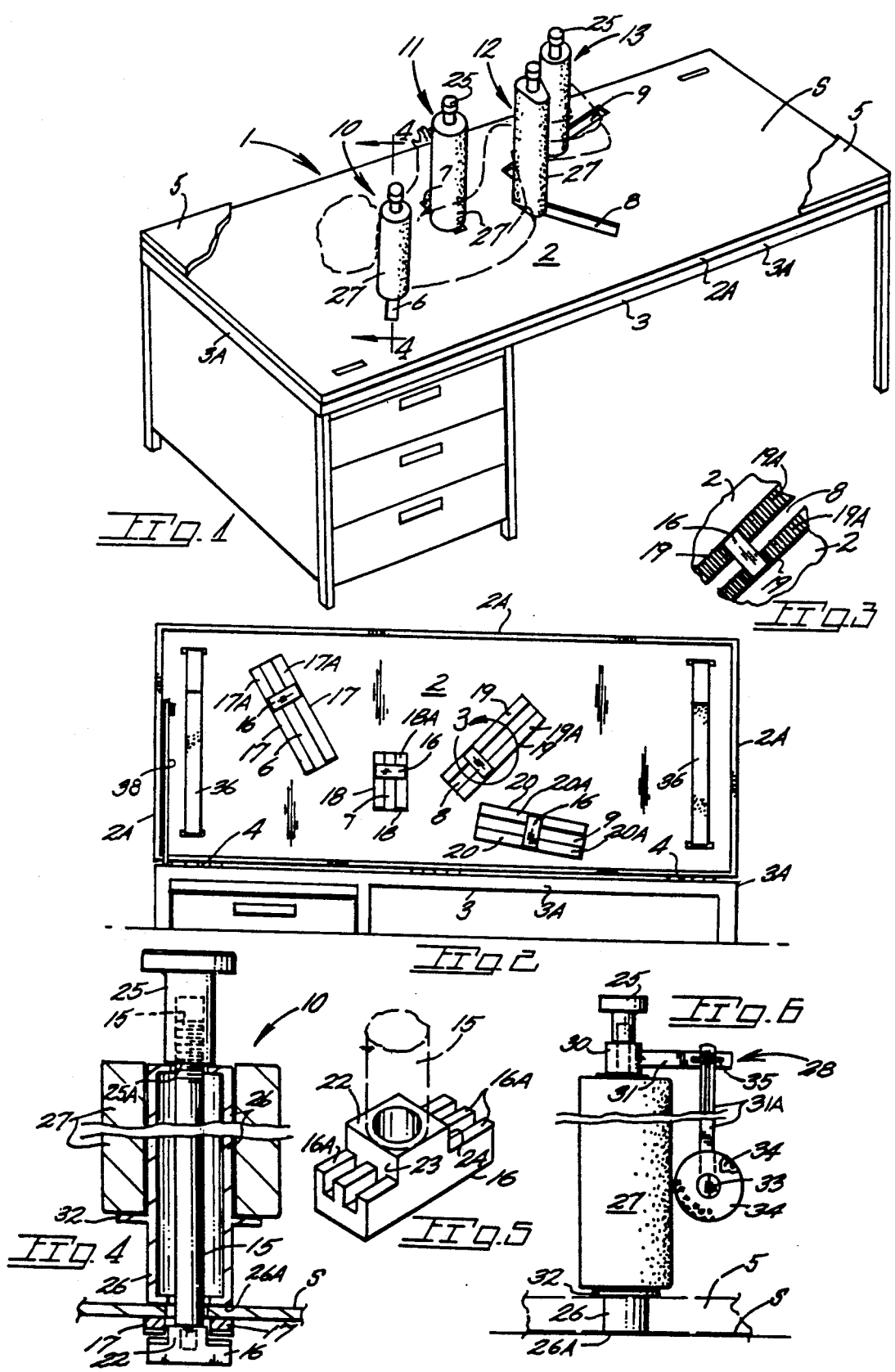

MEDICAL TREATMENT TABLE WITH PASSIVE RESTRAINTS

BACKGROUND AND SUMMARY OF THE INVENTION

The present invention pertains to tables for use in the medical field which restrain a patient in place during treatment.

A problem exists in administering treatments to patients particularly where the treatment results in some degree of pain. Certain treatments, for example, in taking bone marrow specimens are painful and can result in complications if the patient moves during the procedure. The problem of immobilizing a patient is accentuated when the patient is a child. Further, the use of restraints such as straps when treating children is particularly unsuitable.

The present invention is embodied in a table having several positionable abutments thereon which immobilize the patient in a desired position.

The table utilizes a top surface having openings therein to permit positioning of post assemblies to accommodate a wide range of individual shapes and sizes to assure retention of the person in the position desired for the duration of the procedure being performed.

Post assemblies are positionable along the table top surface and are adjustable for a range of children and adult sizes and for various positions. Provision is made for secure attachment of the post assemblies to the table in view of the loads imparted against same by the patient. The post assemblies are provided with a lock operable by a control at the exposed end of the assembly. A foot member on the post assembly engages the table to prevent accidental displacement of the post assembly by a patient during a medical procedure. A secondary restraint is in the form of a post appendage and inhibits vertical movement of the patient's torso and lower legs.

Important objectives include the provision of a treatment table which is conducive to immobilizing a patient without the use of objectionable straps and other objectionable arresting devices; the provision of a medical treatment table which utilizes multiple positionable post assemblies to confine and immobilize a patient in a position for a particular medical procedure; the provision of a medical table readily altered by personnel to accommodate a wide range of torso sizes and retain same in the position required for a specific medical procedure.

BRIEF DESCRIPTION OF THE DRAWINGS

In the accompanying drawings:

FIG. 1 is a perspective view of the present table shown in use with a patient thereon shown in broken lines;

FIG. 2 is a fragmentary front elevational view of the table with a table top member raised to disclose the underside thereof;

FIG. 3 is an enlarged fragmentary view of that structure encircled at 3 in FIG. 2;

FIG. 4 is a vertical sectional view taken along line 4—4 of FIG. 1;

FIG. 5 is a perspective view of a foot member of a post assembly; and

FIG. 6 is an elevational view of a post assembly equipped with a secondary restraint.

DETAILED DESCRIPTION OF THE PREFERRED EMBODIMENTS

With continuing attention to the drawings wherein applied reference numerals indicate parts similarly hereinafter identified, the reference numeral 1 indicates generally the present table which may include drawers for storage purposes.

The table structure includes a top member 2 of rectangular shape in place on a top support member 3 with hinges at 4. Perimetrical walls at 2A and 3A abut one another edgewise to provide an internal space or area between top 2 and support member 3.

Top member 2 includes an upper surface S on which a pad 5 is placed for purposes of comfort. Formed in top member 2 are non-parallel openings 6, 7, 8 and 9 which preferably are of elongate shape. Corresponding openings are provided in pad 5.

Restraint assemblies are indicated generally at 10, 11, 12 and 13 and are positionable and lockable as later explained to abut the patient's neck and shoulder area, the lower abdomen, the posterior portions of the knees and the anterior portions of the ankles.

A typical restraint assembly includes, per FIG. 4, a shaft 15 equipped with a foot as at 16 for engagement with pairs of retainers 17, 18, 19 and 20 arranged along the opposite sides of openings 6, 7, 8 and 9 and on the underside of top member 2. To retain shaft 15 against lateral movement, the foot thereon and a pair of retainers are provided with irregular surfaces such as interengageable teeth as at 16A (on foot 16) and as at 17A, 18A, 19A and 20A. If so desired, each foot member 16 and the retainers may be otherwise equipped with other friction enhancing means to prevent lateral post displacement, as for example, pins and sockets on each foot and retainer.

In a typical foot 16 a boss at 22 projects upwardly with boss side walls 23-24 slidably engaging parallel edges of the table top openings and the opposed edges of a pair of retainers along the edges to confine the foot against rotation. Vertical positioning of the foot is by actuation of a control knob 25 in threaded engagement with shaft 15 with the knob lower end 25A bearing on the upper end of a spacer tube 26, the lower end of which at 26A rests on table surface S. Tube 26 carries an elongate cushion 27. Accordingly, rotation of control knob 25 serves to lift and lower foot 16 into and out of locking engagement with the retainers on the underside of table top member 2. A ring at 32 on tube 26 serves to support sleeve the shaped cushion 27 of resilient material above the surface of table pad 5.

To confine the upper torso and the legs in place against upward movement, it has proved desirable to provide a secondary restraint assembly shown as an appendage generally at 28 in FIG. 6 on certain of the above described restraint assemblies. Such an appendage includes a collar 30 with an arm 31 with a secondary arm at 31A provided with a cross member 33 at its lower or distal end. Cushions at 34 are on cross member 33. A fastener assembly 35 permits arm 32 to be adjusted vertically as well as angularly relative horizontal arm 31. This secondary restraint has proved beneficial when used on neck and shoulder restraint assembly 10 and ankle restraint assembly 13 to prevent undesired upward movement.

The cushions 27 may vary in cross sectional shape, as for example, the restraint assembly generally at 12 utilizes a non-circular cushion for engagement with posterior portions of the knees.

In use, the various restraint assemblies 10-13 are readily positioned by actuation of their control knobs 25 to lower their respective foot members 16 permitting horizontal positioning of the restraint assemblies and subsequent locking of same in place by rotation of the control knob 25 to lift the foot member into engagement with a pair of retainers 16-20.

For the sake of convenience, a brace at 38 serves to maintain table top 2 upright, as for example, when straps at 36 are being joined which serve to hold pad 5 in place on the table top member. The straps 36 may be provided with fabric closure means to facilitate changing of a pad 5.

While we have shown but one embodiment of the invention, it will be apparent to those skilled in the art that the invention may be embodied still otherwise without departing from the spirit and scope of the invention.

Having thus described the invention, what is desired to be secured by a Letters Patent is:

1. A passive restraint table for supporting and immobilizing a patient's torso during medical treatment, said table comprising,
   a horizontal table top member defining multiple non-parallel openings therein, and
   upright restraint assemblies extending one each through said openings, each of said assemblies including a shaft, a foot on said shaft upwardly engageable with the table top member, said foot including an irregular surface, an elongate cushion disposed about said shaft, a control on said shaft for imparting axial movement to said shaft to vertically position said foot into and out of engagement with the underside of the table top member to lock the shaft against horizontal displacement.

2. The table claimed in claim 1 wherein said openings in the table top member are elongate to permit lateral positioning of a post of a restraint assembly to accommodate a range of torso sizes and positions.

3. The table claimed in claim 1 wherein said restraint assembly additionally includes a spacer tube concentric with said post, said post and said control are in threaded engagement with rotation of said control in one direction imparting lifting movement to said foot for engagement with said underside of the table top member.

4. The restraint table claimed in claim 1 wherein said horizontal table top member includes retainers disposed on the underside thereof, said foot engageable with said retainers.

5. The restraint table claimed in claim 4 wherein said retainers and said foot are of toothed configuration for locking engagement with said foot.

6. The restraint table claimed in claim 1 additionally including a secondary restraint assembly in place on said post.

7. The restraint table claimed in claim 6 wherein said secondary restraint assembly includes first and second arms, means adjustably joining said first and second arms, a resilient member carried by said arms for contact with the patient's body.

8. A passive restraint table for immobilizing a patient, said table comprising
   a horizontal table top member defining openings therein, and
   upright restraint assemblies extending one each through said openings, each of said assemblies including a shaft, a foot on said shaft upwardly engageable with the table top member, an elongate cushion disposed about said shaft, a control on said shaft for imparting axial movement to said shaft to vertically position said foot into and out of engagement with the table top member to lock the shaft against horizontal displacement, a spacer tube concentric with the post, said post and said control are in threaded engagement with rotation of said control in one direction imparting lifting movement to said foot for foot engagement with the underside of the table top member.

9. The restraint table claimed in claim 8 additionally including a secondary restraint assembly in place on said shaft, said secondary restraint assembly including first and second arms, means adjustably joining said first and second arms, a resilient member carried by said arms for contact with the patient's body.

* * * * *